United States Patent
Bogan, Jr. et al.

(10) Patent No.: US 7,049,466 B2
(45) Date of Patent: May 23, 2006

(54) RECYCLE PROCESS

(75) Inventors: Leonard Edward Bogan, Jr., Hatfield, PA (US); Daniel A. Bors, Maple Glen, PA (US); Fernando Antonio Pessoa Cavalcanti, Lafayette Hill, PA (US); Scott Han, Lawrenceville, NJ (US); Bradley Anson Jacobs, Chalfont, PA (US); Frederick William Kaiser, Fort Washington, PA (US); Peter David Klugherz, Huntingdon Valley, PA (US); Manhua Lin, Maple Glen, PA (US); Donald Lee Zolotorofe, Ivyland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 421 days.

(21) Appl. No.: 09/962,998

(22) Filed: Sep. 25, 2001
(Under 37 CFR 1.47)

(65) Prior Publication Data
US 2002/0123647 A1    Sep. 5, 2002

Related U.S. Application Data

(60) Provisional application No. 60/236,142, filed on Sep. 29, 2000.

(51) Int. Cl.
*C07C 51/16* (2006.01)

(52) U.S. Cl. ........................ 562/549; 558/319

(58) Field of Classification Search .............. 562/512, 562/512.2, 521, 522, 523, 542, 545, 546, 562/547, 598

See application file for complete search history.

(56) References Cited

U.S. PATENT DOCUMENTS

| | | | |
|---|---|---|---|
| 5,049,692 A | 9/1991 | Hatano et al. | |
| 5,281,745 A | 1/1994 | Ushikubo et al. | |
| 5,380,933 A | 1/1995 | Ushikubo et al. | |
| 5,430,209 A | 7/1995 | Agaskar et al. | |
| 5,430,210 A | 7/1995 | Grasselli et al. | |
| 5,532,384 A | 7/1996 | Shirley et al. | |
| 5,705,684 A * | 1/1998 | Hefner et al. ............... | 562/545 |
| 5,726,327 A | 3/1998 | Acharya et al. | |
| 5,994,580 A | 11/1999 | Takahashi et al. | |

FOREIGN PATENT DOCUMENTS

| | | |
|---|---|---|
| DE | 199 10 507 A1 | 9/2000 |
| EP | 0 484 136 B1 | 5/1992 |
| EP | 0 495 504 B1 | 7/1992 |
| EP | 0 585 023 A1 | 3/1994 |
| EP | 0 608 838 A2 | 8/1994 |
| EP | 0 962 253 A2 | 12/1999 |
| EP | 962 253 * | 12/1999 |
| EP | 0 997 454 A1 | 5/2000 |
| JP | 7-53448 | 2/1995 |
| WO | WO 97/36849 | 10/1997 |
| WO | WO 00/09260 | 2/2000 |
| WO | WO 00/10957 | 3/2000 |
| WO | WO 00/29105 | 5/2000 |
| WO | WO 00/29106 | 5/2000 |

* cited by examiner

*Primary Examiner*—Johann Richter
*Assistant Examiner*—Karl Puttlitz
(74) *Attorney, Agent, or Firm*—Alan Holler; Marcella Bodner

(57) ABSTRACT

A method for producing an unsaturated carboxylic acid comprises: (a) contacting, in a reaction zone, an alkane with a catalyst containing a mixed metal oxide, under conditions which produce a product gas comprising the unsaturated carboxylic acid, unreacted alkane and a product alkene; (b) recovering unreacted alkane and product alkene from the product gas; and (c) recycling the recovered unreacted alkane and product alkene to the reaction zone; wherein the mixed metal oxide consists of a material having the formula $$A_aM_mN_nX_xO_o$$

wherein A is at least one element selected from the group consisting of molybdenum and tungsten, wherein M is at least one element selected from the group consisting of vanadium, cerium and chromium, wherein N is at least one element selected from the group consisting of tellurium, bismuth and selenium, wherein X is at least one element selected from the group consisting of niobium, tantalum, titanium, aluminum, zirconium, chromium, manganese, iron, ruthenium, cobalt, rhodium, nickel, platinum, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium, wherein $0.25 < a < 0.98$, $0.003 < m < 0.5$, $0.003 < n < 0.5$, $0.003 < x < 0.5$ and o is dependent on the oxidation state of the other elements. An analogous method for the preparation of unsaturated nitriles is also disclosed.

14 Claims, No Drawings

RECYCLE PROCESS

CROSS REFERENCE TO RELATED PATENT APPLICATIONS

This is a non-provisional application of prior pending U.S. provisional application Ser. No. 60/236,142 filed on Sep. 29, 2000.

The present invention relates to a method for producing unsaturated carboxylic acids by subjecting alkanes to vapor phase catalytic oxidation wherein unreacted alkanes and alkenes formed during the reaction are recycled to the vapor phase catalytic oxidation.

The present invention also relates to a method for producing unsaturated nitriles by subjecting alkanes to vapor phase catalytic oxidation in the presence of ammonia wherein unreacted alkanes and alkenes formed during the reaction are recycled to the vapor phase catalytic oxidation.

Nitriles, such as acrylonitrile and methacrylonitrile, have been industrially produced as important intermediates for the preparation of fibers, synthetic resins, synthetic rubbers, and the like. The most popular method for producing such nitriles is to subject an olefin such as propene or isobutene to a catalytic reaction with ammonia and oxygen in the presence of a catalyst in a gaseous phase at high temperature. Known catalysts for conducting this reaction include a Mo—Bi—P—O catalyst, a V—Sb—O catalyst, an Sb—U—V—Ni—O catalyst, an Sb—Sn—O catalyst, a V—Sb—W—P—O catalyst and a catalyst obtained by mechanically mixing a V—Sb—W—O oxide and a Bi—Ce—Mo—W—O oxide. However, in view of the price difference between propane and propene or between isobutane and isobutene, attention has been drawn to the development of a method for producing acrylonitrile or methacrylonitrile by a so-called ammoxidation reaction wherein a lower alkane, such as propane or isobutane, is used as starting material, and it is catalytically reacted with ammonia and oxygen in a gaseous phase in the presence of a catalyst.

In particular, U.S. Pat. No. 5,281,745 discloses a method for producing an unsaturated nitrile comprising subjecting an alkane and ammonia in the gaseous state to catalytic oxidation in the presence of a catalyst which satisfies the conditions:

(1) the mixed metal oxide catalyst is represented by the empirical formula $$Mo_aV_bTe_cX_xO_n$$

wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium; and, when a=1, b=0.01 to 1.0, c=0.01 to 1.0, x=0.01 to 1.0 and n is a number such that the total valency of the metal elements is satisfied; and (2) the catalyst has X-ray diffraction peaks at the following angles (±0.3° C.) of 2θ in its X-ray diffraction pattern: 22.1°, 28.2°, 36.2°, 45.2° and 50.0°.

There is no disclosure, whatsoever, of the use of a recycle process.

Similarly, Japanese Laid-Open Patent Application No. 6-228073 discloses a method of nitrile production comprising reacting an alkane in a gas phase contact reaction with ammonia in the presence of a mixed metal oxide catalyst of the formula $$W_aV_bTe_cX_xO_n$$

wherein X represents one or more elements selected from niobium, tantalum, titanium, aluminum, zirconium, chromium, manganese, iron, ruthenium, cobalt, rhodium, nickel, palladium, platinum, antimony, bismuth, indium and cerium; and, when a=1, b=0.01 to 1.0, c=0.01 to 1.0, x=0.01 to 1.0 and n is determined by the oxide form of the elements.

There is no disclosure, whatsoever, of the use of a recycle process.

Unsaturated carboxylic acids such as acrylic acid and methacrylic acid are industrially important as starting materials for various synthetic resins, coating materials and plasticizers. Commercially, the current process for acrylic acid manufacture involves a two-step catalytic oxidation reaction starting with a propene feed. In the first stage, propene is converted to acrolein over a modified bismuth molybdate catalyst. In the second stage, acrolein product from the first stage is converted to acrylic acid using a catalyst composed of mainly molybdenum and vanadium oxides. In most cases, the catalyst formulations are proprietary to the catalyst supplier, but, the technology is well established. Commercial incentives exist for producing acrylic acid using a lower cost propane feed. Therefore, the prior art describes cases wherein a mixed metal oxide catalyst is used to convert propane to acrylic acid in one step.

In particular, U.S. Pat. No. 5,380,933 discloses a method for producing an unsaturated carboxylic acid comprising subjecting an alkane to a vapor phase catalytic oxidation reaction in the presence of a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components exclusive of oxygen, satisfy the following relationships:

0.25<r(Mo)<0.98, 0.003<r(V)<0.5, 0.003<r(Te)<0.5 and 0.003<r(X)<0.5, wherein r(Mo), r(V), r(Te) and r(X) are the molar fractions of Mo, V, Te and X, respectively, based on the total amount of the essential components exclusive of oxygen.

There is no disclosure, whatsoever, of the use of a recycle process.

Japanese Laid-Open Patent Application No. 07-053448 discloses the preparation of acrylic acid by the gas-phase catalytic oxidation of propene in the presence of a mixed metal oxide catalyst of the formula $$Mo_aV_bTe_cX_dO_n$$

wherein X is at least one element selected from Nb, Ta, W, Ti, Al, Zr, Cr, Mn, Fe, Ru, Co, Rh, Ni, Pd, Pt, Sb, Bi, B, In, Li, Na, K, Rb, Cs and Ce; a=0.25–0.98; b=0.003–0.5; c=0.003–0.5; d=0.003–0.5 and n is determined by the oxidation state of the other elements.

Similarly, Published International Application No. WO 2000/09260 discloses a catalyst for the selective oxidation of propene to acrylic acid and acrolein which comprises a mixed metal oxide of molybdenum, vanadium, lanthanum, palladium niobium, and copper and/or chromium wherein the metals are present in the ratios given by the formula $$Mo_aV_bLa_cPd_dNb_eX_f$$

wherein X=Cu and/or Cr; a=1; b=0.01 to 0.9; c=greater than zero to 0.22; d=0.0000001 to 0.2; e=0 to 0.2; and f=0 to 0.2.

Published International Application No. WO 2000/29105 discloses an improved catalyst system for the oxidation of alkanes and alkenes having a calcined composition of

wherein X is at least one element selected from the group consisting of La, Te, Ge, Zn, Si, In and W; a is 1; b is 0.01 to 0.9; c is >0 to 0.2; d is 0.0000001 to 0.2; e is >0 to 0.2; and f is >0 to 0.5. The elements are preferably present in combination with oxygen in the form of various oxides.

Published International Application No. WO 2000/29106 discloses an improved catalyst system for the selective oxidation of propane having a calcined composition of

wherein X is at least one element selected from the group consisting of La, Te, Ge, Zn, Si, In and W; a is 1; b is 0.01 to 0.9; c is >0 to 0.2; d is 0.0000001 to 0.2; e is >0 to 0.2; and f is >0 to 0.5. The elements are preferably present in combination with oxygen in the form of various oxides Both European Patent Specification No. 0 484 136 B1 and U.S. Pat. No. 5,726,327 disclose that certain petrochemicals (i.e. hydrocarbon derivatives) are produced commercially by the partial oxidation of an appropriate hydrocarbon in the vapor phase over a suitable catalyst in the presence of an oxygen-containing gas. As an example, the references note that cyclic anhydrides are produced commercially by the vapor phase catalytic partial oxidation of aromatic hydrocarbons, such as o-xylene or benzene, or straight-chain hydrocarbons, such as n-butane or butene, in the presence of an oxygen-containing gas over a vanadium-containing catalyst. Similarly, the references note that nitriles, alkylene oxides, aldehydes and halogenated hydrocarbons are produced by the partial oxidation of appropriate alkanes or alkenes in the presence of selected catalysts. Air is generally used as the oxygen-containing gas because of its low cost and ready availability. The reaction(s) can be carried out in any suitable reactor, such as a fixed bed reactor, fluidized bed reactor, moving bed reactor, trickle bed reactor or transport bed reactor, and it produces the hydrocarbon derivative and, generally, carbon monoxide (CO), carbon dioxide ($CO_2$), water and smaller amounts of other partially oxidized by-products. The reaction equipment train generally consists of a reactor, in which the hydrocarbon derivative is produced, a scrubber, in which the hydrocaron derivative is scrubbed from the reactor effluent gases by means of water or some other solvent for the hydrocarbon derivative and some means for further treating the scrubbed effluent gases.

Both of these references go on to indicate that it is common to practice the above-described process(es) on a single pass basis with the conversion of hydrocarbon to the desired petrochemical product being maximized. This results in a low overall efficiency since the selectivity to the petrochemical product is below the maximum. Consequently, the scrubber effluent gas contains considerable amounts of CO and $CO_2$, in addition to unreacted hydrocarbon. These products are usually incinerated, so that the only return realized from them is heat value. In modified processes, a portion of the scrubber effluent gas is recycled, the conversion of the hydrocarbon feedstock is lowered and the selectivity of the hydrocarbon conversion to the desired petrochemical product is increased. The remainder of the effluent is purged from the system to prevent the build-up of CO, $CO_2$ and nitrogen (introduced into the system when air is used as the source of oxygen). These improvements result in a reduced "per pass" conversion, but the overall yield of the process is increased.

However, neither of these references disclose the aforementioned technique(s) in the context of the partial oxidation of alkanes to unsaturated acids or unsaturated nitriles using a mixed metal oxide as is contemplated by the present invention. In fact, European Patent Specification No. 0 484 136 B1 is directed to a process for the production of a hydrocarbon derivative comprising: (a) contacting in a reaction zone a hydrocarbon and an oxygen-containing gas in the presence of an appropriate oxidation catalyst and an inert diluent under conditions which produce a gaseous product containing the hydrocarbon derivative and carbon monoxide; (b) removing the hydrocarbon derivative from the gaseous product; (c) converting carbon monoxide in the gaseous product to carbon dioxide, thereby producing a carbon monoxide-depleted gas stream; (d) removing part of the carbon dioxide from the carbon monoxide-depleted gas stream; and (e) recycling the carbon monoxide-depleted gas stream remaining after step (d) to the reaction zone. This process is exemplified, among other reactions, by a simulation of a two-stage, vapor-phase, acrylic acid from propene production run utilizing a vapor phase hydrocarbon reactor containing a first fixed catalyst bed of bismuth molybdate and a second fixed bed of mixed molybdenum-tungsten-vanadium catalyst, wherein propylene is converted to acrolein in the first bed and then further oxidized to acrylic acid in the second bed.

On the other hand, U.S. Pat. No. 5,726,327 is directed to a process comprising: (a) contacting a hydrocarbon with air in a reaction zone in the presence of an appropriate oxidation catalyst under conditions which produce a product gas comprising a desired petrochemical, unreacted hydrocarbon and moisture; (b) removing the petrochemical from the product gas in a petrochemical recovery zone, thereby producing a petrochemical-free gas stream containing unreacted hydrocarbon; (c) subjecting at least part of the petrochemical-free gas remaining after step (b) to a temperature swing adsorption process comprising: (1) passing at least part of the petrochemical-free gas stream through a hydrocarbon-selective adsorbent, thereby adsorbing unreacted hydrocarbon onto the adsorbent and producing a hydrocarbon-depleted waste gas, and (2) at least partially regenerating the hydrocarbon-selective adsorbent by passing compressed, heated purge air therethrough, thereby producing a gaseous stream comprising desorbed hydrocarbon and purge air; and (d) recycling at least part of the gaseous stream comprising desorbed hydrocarbon and air to the reaction zone, thereby providing at least part of the air used in step (a).

Published International Patent Application No. WO 97/36849 discloses improved continuous processes for the conversion of alkanes such as, for example, propane, to unsaturated aldehydes such as, for example, acrolein, and acids such as, for example, acrylic acid. In these processes, an alkane having from 2 to 8 carbon atoms per molecule, e.g., propane, is first converted to an alkene having the same number of carbon atoms as the alkane, e.g., propylene, and then the alkene is converted to an unsaturated aldehyde having the same number of carbon atoms as the alkene, e.g., acrolein. The aldehyde is then converted to an unsaturated carboxylic acid having the same number of carbon atoms as the aldehyde, e.g., acrylic acid. By operating at low propane-to-propylene conversion, in accordance with the disclosed invention, the selectivity to propylene can be made high, e.g., between 80 and 100%. Since the presence of propane has been found to enhance the efficiency of the propylene-to-acrolein reaction, the low propane conversion is not detrimental to the process. Even though the feed to the acrolein reactor may contain propylene in low concentrations, e.g., 5 to 20 mole %, the low-conversion, high-selectivity mode of operation can be highly efficient provided unreacted propane is recycled to the propane oxidation reactor. Recycle operation is particularly feasible in accordance with the disclosed invention because oxydehydrogenation catalysts, which are preferred for use in the disclosed invention are substantially unaffected by species such as carbon oxides and water which are formed in the acrolein reactor. Hence, after recovery of the acrolein, the non-condensed gases containing propane may be recycled without significant, additional purification steps.

Similarly, European Published Patent Application No. 0 963 788 A2 discloses the preparation of acrylic acid using a three-step process wherein propane is converted to propene in a first reactor using a first catalyst, propene is converted to acrolein in a second reactor using a second catalyst and acrolein is converted to acrylic acid in a third reactor using a third catalyst. The product gas from the third reactor is fed to an absorption column to allow absorption of the condensed component and the uncondensed gas flowing from the absorption column is fed to the inlet of the first reactor.

U.S. Pat. No. 5,994,580 discloses a process for producing acrylic acid from propane and oxygen gas through a vapor phase catalytic oxidation reaction, the process comprising conducting the reaction using as a catalyst a metal oxide containing metallic elements Mo, V, Sb and A wherein A is at least one element selected from the group consisting of Nb, Ta, Sn, W, Ti, Ni, Fe, Cr and Co. In the production of acrylic acid from propane, the reaction yields by-products such as, e.g., propylene, carbon monoxide, carbon dioxide and acetic acid, besides acrylic acid as the target compound. These by-products can be separated from the acrylic acid by a purification operation based on the differences in boiling point, e.g., distillation. Among the by-products, the isolated propylene, which serves as an intermediate for acrylic acid, can be utilized again in the reaction after being mixed with feedstock propane. In this case, however, the propylene is desirably mixed in an amount up to 20 volume % based on the propane so as to avoid adverse influences on the reaction.

European Patent Specification No. 0 495 504 B1 discloses a process for producing methacrylic acid, which comprises the steps of: (A) subjecting isobutane to gas phase oxidation with molecular oxygen in the presence of a solid catalyst to obtain a reaction product gas containing methacrylic acid, methacrolein, acetic acid, water, unreacted isobutane, oxygen, carbon monoxide and carbon dioxide; (B) separating the reaction product gas into a condensible component containing methacrylic acid, methacrolein, acetic acid and water and a non-condensible gas component containing unreacted isobutane, oxygen, carbon monoxide and carbon dioxide; (C) catalytically oxidizing the carbon monoxide in the non-condensible gas component with oxygen to convert it into carbon dioxide; (D) removing the carbon dioxide in the non-condensible gas component; and (E) recycling the non-condensible gas component which has passed through the steps (C) and (D) in the step (A); wherein the order of carrying out the step (C) and the step(D) is reversible.

European Published Patent Application No. 0 585 023 A1 and U.S. Pat. No. 5,532,384 disclose a process for the production of a partial oxidation product selected from cyclic anhydrides, alkylene oxides, halogenated hydrocarbons, aldehydes, unsaturated carboxylic acids, unsaturated nitriles and mixtures of two or more thereof comprising: (a) contacting, in the vapor phase, in a reaction zone, a hydrocarbon containing 2 to 12 carbon atoms with an oxygen-rich gas in the presence of an appropriate oxidation catalyst under conditions which produce a gaseous stream containing the partial oxidation product; (b) removing the partial oxidation product from the gaseous product stream; (c) flowing substantially all of the resulting gaseous stream free of the partial oxidation product, at superatmospheric pressure, through an adsorption bed containing an adsorbent which is selective for hydrocarbons containing 2 to 12 carbon atoms, thereby removing unreacted hydrocarbon from the resulting gaseous stream; (d) terminating the flow of the resulting gaseous stream through the adsorption bed when the unreacted hydrocarbon front reaches a predetermined point in the adsorption bed, and depressurizing the adsorption bed, thereby desorbing unreacted hydrocarbon from the adsorption bed; (e) passing a nitrogen-rich gas through the adsorption bed, thereby further desorbing unreacted hydrocarbon from the adsorption bed; and (f) passing the desorbed unreacted hydrocarbon and the nitrogen-rich gas to the reaction zone.

U.S. Pat. No. 5,430,209 discloses a process for converting an alkane of the formula $C_nH_{2n+2}$ to an alkene of the formula $C_nH_{2n}$ where n is the same for the alkane and the alkene and n is from 2 to 5, the process comprising the steps of: (a) contacting the alkane with a solid material comprising a dehydrogenation catalyst under conditions sufficient to produce the alkene and $H_2$; (b) contacting the effluent from step (a) with a reducible metal oxide under conditions sufficient to selectively convert the $H_2$ and reducible metal oxide to a reduced form of the metal oxide and water; and (c) contacting at least a portion of the effluent of step (b) with a solid material comprising a dehydrogenation catalyst under conditions sufficient to convert unreacted alkane to additional quantities of the alkene and $H_2$.

U.S. Pat. No. 5,430,210 discloses a process for converting an alkane of the formula $C_nH_{2n+2}$ to an alkene of the formula $C_nH_{2n}$ where n is the same for the alkane and the alkene and n is from 2 to 5, the process comprising the steps of: (a) contacting the alkane with a solid material comprising a dehydrogenation catalyst under conditions sufficient to produce the alkene and $H_2$; (b) contacting a first stream comprising effluent from step (a) and a second stream comprising oxygen with separate surfaces of a membrane impervious to non-oxygen containing gases under conditions sufficient to selectively convert the $H_2$ to water, wherein the membrane comprises a metal oxide selective for hydrogen combustion; and (c) contacting at least a portion of effluent from step (b) with a solid material comprising a dehydrogenation catalyst under conditions sufficient to convert unreacted alkane to additional quantities of alkene and $H_2$.

U.S. Pat. No. 5,705,684 discloses a process for preparing acrolein, acrylic acid or a mixture thereof from propane, in which: (A) in a first stage A, the propane is subjected to a partial heterogeneously catalyzed dehydrogenation in the gas phase to give propylene; (B) the product gas mixture from stage A containing propylene and unreacted propane is used in a second stage B as feed to an oxidation reactor and in the oxidation reactor the propylene is subjected to a selective heterogeneously catalyzed gas-phase partial oxidation with molecular oxygen to give acrolein, acrylic acid or a mixture thereof as target product, with pure oxygen being used as oxygen source; and (C) in a third stage C, the target product is separated from the product gas stream obtained from the partial oxidation of the propylene in stage B and at least the unreacted propane present in the product gas stream from stage B is recirculated to the dehydrogenation stage A, wherein from among the constituents other than propane and propylene present in the product gas mixture from stage A, at least the hydrogen and the water vapor are separated from the product gas mixture before it is used as feed to the oxidation reactor of the second stage B.

It has now been determined that the presence of a minor amount of alkene, such as, for example, propene, in an alkane feed stream, such as, for example, a propane feed stream, of a vapor phase catalytic oxidation of alkane can significantly increase the selectivity to a desired product, as compared to the case where no alkene is present, when using a catalyst containing a mixed metal oxide as hereinafter defined. Moreover, it has further been determined that alkene produced as a by-product of a vapor phase catalytic oxidation of alkane when using a catalyst containing a mixed metal oxide as hereinafter defined can be recycled to the reactor in conjunction with unreacted and make-up alkane to achieve the aforementioned increase in selectivity. Thus, increased selectivity can be achieved via the presence of alkene without actually having to provide fresh alkene.

Thus, in a first aspect, the present invention provides a method for producing an unsaturated carboxylic acid comprising: (a) contacting, in a reaction zone, an alkane with a catalyst containing a mixed metal oxide, under conditions which produce a product gas comprising the product unsaturated carboxylic acid, unreacted alkane and a product alkene; (b) recovering unreacted alkane and product alkene from the product gas; and (c) recycling the recovered unreacted alkane and product alkene to the reaction zone; wherein the mixed metal oxide consists of a material having the formula $$A_a M_m N_n X_x O_o$$

wherein A is at least one element selected from the group consisting of molybdenum and tungsten, wherein M is at least one element selected from the group consisting of vanadium and cerium, wherein N is at least one element selected from the group consisting of tellurium and selenium, wherein X is at least one element selected from the group consisting of niobium, tantalum, titanium, aluminum, zirconium, chromium, manganese, iron, ruthenium, cobalt, rhodium, nickel, platinum, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium; and wherein $0.25<a<0.98$, $0.003<m<0.5$, $0.003<n<0.5$, $0.003<x<0.5$ and o is dependent on the oxidation state of the other elements.

In a second aspect, the present invention provides a method for producing an unsaturated nitrile comprising: (a) contacting, in a reaction zone, an alkane and ammonia in the presence of a catalyst containing a mixed metal oxide, under conditions which produce a product gas comprising the product unsaturated nitrile, unreacted alkane and a product alkene; (b) recovering unreacted alkane and product alkene from the product gas; and (c) recycling the recovered unreacted alkane and product alkene to the reaction zone; wherein the mixed metal oxide has the formula $$A_a M_m N_n X_x O_o$$

wherein A is at least one element selected from the group consisting of molybdenum and tungsten, wherein M is at least one element selected from the group consisting of vanadium and cerium, wherein N is at least one element selected from the group consisting of tellurium, antimony and selenium, wherein X is at least one element selected from the group consisting of niobium, tantalum, titanium, aluminum, zirconium, chromium, manganese, iron, ruthenium, cobalt, rhodium, nickel, platinum, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium; and wherein $0.25<a<0.98$, $0.003<m<0.5$, $0.003<n<0.5$, $0.003<x<0.5$ and o is dependent on the oxidation state of the other elements.

The mixed metal oxide to be used as a catalyst component in the first aspect of the present invention consists of a material having the formula $$A_a M_m N_n X_x O_o$$

wherein A is at least one element selected from the group consisting of molybdenum and tungsten, wherein M is at least one element selected from the group consisting of vanadium and cerium, preferably vanadium, wherein N is at least one element selected from the group consisting of tellurium, and selenium, preferably tellurium, wherein X is at least one element selected from the group consisting of niobium, tantalum, titanium, aluminum, zirconium, chromium, manganese, iron, ruthenium, cobalt, rhodium, nickel, platinum, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium, preferably niobium, tantalum and zirconium, most preferably niobium.

The mixed metal oxide to be used as a catalyst component in the second aspect of the present invention has the formula $$A_a M_m N_n X_x O_o$$

wherein A is at least one element selected from the group consisting of molybdenum and tungsten, wherein M is at least one element selected from the group consisting of vanadium and cerium, preferably vanadium, wherein N is at least one element selected from the group consisting of tellurium, antimony and selenium, preferably tellurium, wherein X is at least one element selected from the group consisting of niobium, tantalum, titanium, aluminum, zirconium, chromium, manganese, iron, ruthenium, cobalt, rhodium, nickel, platinum, bismuth, boron, indium arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium, preferably niobium, tantalum and zirconium, most preferably niobium.

The proportions of the respective components of the aforementioned mixed metal oxides, based on the total amount of the components, are within the ranges defined by the following relationships: $0.25<a<0.98$, $0.003<m<0.5$, $0.003<n<0.5$, $0.003<x<0.5$ and o is dependent on the oxidation state of the other elements. The ranges represented-by the following relationships are particularly preferred $0.35<a<0.87$, $0.45<m<0.37$, $0.020<n<0.27$, and $0.005<x<0.35$. The value of o, i.e. the amount of oxygen present, is dependent on the oxidation state of the other elements in the catalyst. However, o is typically in the range of from 3 to 4.7.

Particularly preferred mixed metal oxides have the formulae $Mo_aV_mTe_nNb_xO_o$ and $W_aV_mTe_nNb_xO_o$ wherein a, m, n, x and o are as previously defined.

Further, as the mixed metal oxide, one having a certain specific crystal structure is preferred. Specifically, preference is given to the one which exhibits the following five main diffraction peaks at specific diffraction angles 2θ in the X-ray diffraction pattern of the mixed metal oxide (as measured using Cu—Kα radiation as the source):

| X-ray lattice plane | | |
| --- | --- | --- |
| Diffraction angle 2θ (±0.3°) | Spacing medium (Å) | Relative intensity |
| 22.1° | 4.02 | 100 |
| 28.2° | 3.16 | 20~150 |
| 36.2° | 2.48 | 5~60 |
| 45.2° | 2.00 | 2~40 |
| 50.0° | 1.82 | 2~40 |

The intensity of the X-ray diffraction peak may vary depending upon the measuring conditions of each crystal. However, the intensity relative to the peak intensity at 22.1° being 100, is usually within the above ranges. Generally, the peak intensities at 2θ=22.1° and 28.2° are distinctly observed. However, so long as the above five diffraction peaks are observable, the basic crystal structure is the same even if other peaks are observed in addition to the five diffraction peaks, and such a structure is useful for the present invention.

The mixed metal oxides can be prepared in the following manner.

In a first step, a slurry or solution may be formed by admixing metal compounds, preferably at least one of which contains oxygen, and at least one solvent in appropriate amounts to form the slurry or solution. Preferably, a solution is formed at this stage of the catalyst preparation. Generally, the metal compounds contain elements A, M, N, O and X, as previously defined.

Suitable solvents include water, alcohols including, but not limited to, methanol, ethanol, propanol, and diols, etc., as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, as stated above, the amount of water is preferably sufficient to ensure an aqueous solution is formed, and not a slurry, at the time of mixing.

For example, when a mixed metal oxide of the formula $Mo_aV_bTe_cNb_xO_n$, wherein the element A is Mo, the element M is V, the element N is Te and the element X is Nb, is to be prepared, an aqueous solution of telluric acid, an aqueous solution of niobium oxalate and a solution or slurry of ammonium paramolybdate may be sequentially added to an aqueous solution containing a predetermined amount of ammonium metavanadate, so that the atomic ratio of the respective metal elements would be in the prescribed proportions.

Once the aqueous slurry or solution (preferably a solution) is formed, the water is removed by any suitable method, known in the art, to form a catalyst precursor. Such methods include, without limitation, vacuum drying, freeze drying, spray drying, rotary evaporation and air drying. Vacuum drying is generally performed at pressures ranging from 10 mmHg to 500 mmHg. Freeze drying typically entails freezing the slurry or solution, using, for instance, liquid nitrogen, and drying the frozen slurry or solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 40° to 90° C. and at a pressure of from 10 mmHg to 350 mmHg, more preferably at a bath temperature of from 40° C. to 60° C. and at a pressure of from 10 mmHg to 40 mmHg. Air drying may be effected at temperatures ranging from 25° C. to 90° C. Rotary evaporation or air drying are generally preferred.

Once obtained, the catalyst precursor is calcined. The calcination may be conducted in an oxidizing atmosphere, but it is also possible to conduct the calcination in a non-oxidizing atmosphere, e.g., in an inert atmosphere or in vacuo. The inert atmosphere may be any material which is substantially inert, i.e., does not react or interact with the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). However, when the inert atmosphere does flow over the surface of the catalyst precursor, the flow rate can vary over a wide range, e.g., at a space velocity of from 1 to 500 hr$^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired mixed metal oxide.

In a preferred mode of operation, the catalyst precursor is calcined in two stages. In the first stage, the catalyst precursor is calcined in an oxidizing atmosphere (e.g., air) at a temperature of from 200° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 750° C., preferably from 550° C. to 650° C., for from 15 minutes to 8 hours, preferably for from 1 to 3 hours. Optionally, a reducing gas, such as, for example, ammonia or hydrogen, maybe added during the second stage calcination.

In a particularly preferred mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

With calcination, catalysts are formed having the formula $A_aM_mN_nX_xO_o$ wherein A, M, N, X, O, a, m, n, x and o are as previously defined.

The starting materials for the above mixed metal oxides are not limited to those described above. A wide range of materials including, for example, oxides, nitrates, halides or oxyhalides, alkoxides, acetylacetonates and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanasyl acetylacetonate may be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

A mixed metal oxide, thus obtained, exhibits excellent catalytic activities by itself. However, the mixed metal oxide can be converted to a catalyst having higher activities by grinding.

There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned mixed metal oxide, the viscosity, the concentration, etc. of the solvent used in the case of wet grinding, or the optimum conditions of the grinding apparatus. However, it is preferred that grinding is conducted until the average particle size of the ground catalyst precursor would usually be at most 20 μm, more preferably at most 5 μm. Remarkable improvement in the catalytic performance can be observed by grinding to such an extent.

Further, in some cases, it is possible to further improve the catalytic activities by further adding an organic solvent to the ground catalyst precursor to form a slurry, followed by drying again. There is no particular restriction as to the concentration of the slurry, and it is usual to adjust the slurry so that the total amount of the starting material compounds for the ground catalyst precursor is from 10 to 60 wt %. Then, this slurry is dried by a method such as spray drying, freeze drying, evaporation to dryness or vacuum drying, preferably by the spray drying method. Further, similar drying may be conducted also in the case where wet grinding is conducted.

The oxide obtained by the above-mentioned method may be used as a final catalyst, but it may further be subjected to heat treatment usually at a temperature of from 200° to 700° C. for from 0.1 to 10 hours.

The mixed metal oxide thus obtained may be used by itself as a solid catalyst, but may be formed into a catalyst together with a suitable carrier such as silica, alumina, titania, aluminosilicate, diatomaceous earth or zirconia. Further, it may be molded into a suitable shape and particle size depending upon the scale or system of the reactor.

Alternatively, the metal components of the presently contemplated catalyst may be supported on materials such as alumina, silica, silica-alumina, zirconia, titania, etc. by conventional incipient wetness techniques. In one typical method, solutions containing the metals are contacted with the dry support such that the support is wetted; then, the resultant wetted material is dried, for example, at a temperature from room temperature to 200° C. followed by calcination as described above. In another method, metal solutions are contacted with the support, typically, in volume ratios of greater than 3:1 (metal solution:support), and the solution is agitated such that the metal ions are ion-exchanged onto the support. The metal containing support is then dried and calcined as detailed above.

In its first aspect, the method of the present invention comprises subjecting an alkane or a mixture of an alkane and an alkene, to a vapor phase catalytic oxidation reaction in the presence of a catalyst containing the above mixed metal oxide, to produce an unsaturated carboxylic acid.

In the production of such an unsaturated carboxylic acid, it is preferred to employ a starting material gas which contains steam. In such a case, as a starting material gas to be supplied to the reaction system, a gas mixture comprising a steam-containing alkane or a steam-containing mixture of alkane and alkene, and an oxygen-containing gas, is usually used. However, the steam-containing alkane, or the steam-containing mixture of alkane and alkene, and the oxygen-containing gas may be separately and/or alternately be supplied to the reaction system. The steam to be employed may be present in the form of steam gas in the reaction system, and the manner of its introduction is not particularly limited.

Further, as a diluting gas, an inert gas, such as nitrogen, argon or helium, may be supplied. The molar ratio (alkane or mixture of alkane and alkene):(oxygen):(diluting gas):($H_2O$) in the starting material gas is preferably (1):(0.1 to 10):(0 to 20):(0.1 to 70), more preferably (1):(1 to 5.0):(0 to 10):(0.2 to 40).

When steam is supplied together with the alkane, as starting material gas, the selectivity for an unsaturated carboxylic acid is distinctly improved, and the unsaturated carboxylic acid can be obtained from the alkane, in good yield. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas, such as carbon monoxide, carbon dioxide, nitrogen, argon or helium, may be used together with the steam.

In the present invention, as the starting material alkane, it is preferred to employ a $C_{3-8}$ alkane, particularly propane, isobutane or n-butane. As the starting material alkane, propane or isobutane are more preferred. According to the present invention, from such an alkane, an unsaturated carboxylic acid such as an $\alpha,\beta$-unsaturated carboxylic acid can be obtained in good yield. For example, propane or isobutane are used as the starting material, acrylic acid or methacrylic acid will be obtained, respectively, in good yield.

There is no limitation on the source of the alkane.

The detailed mechanism of the oxidation reaction of the present invention is not clearly understood, but the oxidation reaction is carried out by oxygen atoms present in the above mixed metal oxide or by molecular oxygen present in the feed gas. To incorporate molecular oxygen into the feed gas, such molecular oxygen may be supplied by air or oxygen gas. It is preferred to use oxygen gas in recycle operations in order to avoid the need for nitrogen removal.

It is also possible to use only an alkane, substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator, regenerated and then returned to the reaction zone for reuse. As the regeneration method of the catalyst, a method may, for example, be mentioned which comprises contacting an oxidative gas such as oxygen, air or nitrogen monoxide with the catalyst in the regenerator usually at a temperature of from 300° to 600° C.

The first aspect of the present invention will be described in further detail with respect to a case where propane is used as the starting material alkane and air is used as the oxygen source. The reaction system may be a fixed bed system or a fluidized bed system. However, since the reaction is an exothermic reaction, a fluidized bed system may be employed whereby it is easier to control the reaction temperature. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes, the composition of the feed gas may be selected in accordance with the conditions for propane.

Typical reaction conditions for the oxidation of propane or isobutane to acrylic or methacrylic acid may be utilized in the practice of the present invention. General conditions for the process of the present invention are as follows: the reaction temperature can vary from 200° C. to 700° C., but is usually in the range of from 200° to 550° C., more preferably from 250° to 480° C., most preferably 300° C. to 400° C.; the gas space velocity, SV, in the vapor phase reaction is usually within a range of from 100 to 10,000 $hr^{-1}$, preferably from 300 to 6,000 $hr^{-1}$, more preferably from 300 to 2,000 $hr^{-1}$; the average contact time with the catalyst can be from 0.01 to 10 seconds or more, but is usually in the range of from 0.1 to 10 seconds, preferably from 2 to 6 seconds; the pressure in the reaction zone usually ranges from 0 to 75 psig, but is preferably no more than 50 psig.

Of course, in the oxidation reaction of the present invention, it is important that the hydrocarbon and oxygen concentrations in the feed gases be maintained at the appropriate levels to minimize or avoid entering a flammable region within the reaction zone or especially at the outlet of the reactor zone. Generally, it is preferred that the outlet oxygen level be low to minimize after-burning. In addition, operation of the reaction at a low temperature (below 450° C.) is extremely attractive because after-burning becomes less of a problem which enables attainment of higher selectivity to the desired products. The catalyst of the present invention operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as carbon monoxide, carbon dioxide, nitrogen, argon or helium may be employed.

Carbon monoxide, carbon dioxide, acetic acid, etc. may be produced as by-products, in addition to acrylic acid. Further, in the method of the present invention, an unsaturated aldehyde may sometimes be formed depending upon the reaction conditions. In such a case, such an unsaturated aldehyde can be converted to the desired unsaturated carboxylic acid by subjecting it again to the vapor phase catalytic oxidation with the mixed metal oxide-containing catalyst of the present invention or by subjecting it to a vapor phase catalytic oxidation reaction with a conventional oxidation reaction catalyst for an unsaturated aldehyde.

Propene is also formed as a reaction by-product. The unreacted propane and by-product propene are recovered from the effluent stream exiting the gas phase catalytic oxidation reactor and are recycled to the reactor. Recovery of the unreacted propane and by-product propene from the reactor effluent stream may be effected by conventional techniques for the recovery of hydrocarbon streams. For example, acrylic acid and oxygenated by-products of the reaction (including $CO_2$ and CO (after being oxidized to $CO_2$)) may be scrubbed from the effluent stream by utilization of suitable solvent(s) in one or more "scrubbers" or absorption towers; or the hydrocarbon components of the effluent stream may be adsorbed in one or more adsorption beds which selectively adsorb the hydrocarbons and, which subsequently, are desorbed and sent to the reactor feed.

In order to improve the yield over and above that achieved by the use of recycled propene, it is also possible to use a reactor configuration wherein the reactor comprises at least two sub-zones, the sub-zones being disposed sequentially so that the reactants pass through the sub-zones in sequential order. At least two of the sub-zones are at different temperatures. Preferably, the higher temperature is upstream of the lower temperature, i.e. the higher temperature sub-zone precedes the lower temperature sub-zone in the sequence. In this regard, the temperatures may be controlled by providing separate temperature control systems for the at least two sub-zones.

Alternatively, another technique for increasing the yield over and above that achieved by the use of the recycled propene is to once again use a reactor configuration wherein the reactor comprises at least two sub-zones, the sub-zones being disposed sequentially so that the reactants pass through the sub-zones in sequential order. However, in this embodiment, at least two of the sub-zones contain different concentrations of the catalyst containing a mixed metal oxide. Preferably, the lower concentration of catalyst is downstream of the higher concentration of catalyst, i.e. the higher concentration of catalyst sub-zone precedes the lower concentration of catalyst sub-zone in the sequence. In this regard, the concentration of catalyst could be controlled by diluting the catalyst with an inert solid, e.g., physically mixing the catalyst with an inert solid, or, if the catalyst is a supported catalyst, changing the concentration of the catalyst on the support.

In its second aspect, the method of the present invention comprises subjecting an alkane, to a vapor phase catalytic oxidation reaction with ammonia in the presence of a catalyst containing the above mixed metal oxide, to produce an unsaturated nitrile.

In the production of such an unsaturated nitrile, as the starting material alkane, it is preferred to employ a $C_{3-8}$ alkane such as propane, butane, isobutane, pentane, hexane, and heptane. However, in view of the industrial application of nitrites to be produced, it is more preferred to employ a lower alkane having 3 or 4 carbon atoms, particularly propane or isobutane.

There is no limitation on the source of the alkane.

The detailed mechanism of the oxidation reaction of these aspects of the present invention is not clearly understood. However, the oxidation reaction is conducted by the oxygen atoms present in the above mixed metal oxide or by the molecular oxygen in the feed gas. When molecular oxygen is incorporated in the feed gas, the oxygen may be pure oxygen gas. However, since high purity is not required, it is usually economical to use an oxygen containing gas such as air.

As the feed gas, it is possible to use a gas mixture comprising an alkane, ammonia and an oxygen-containing gas. However, gas mixtures comprising an alkane and ammonia, and an oxygen-containing gas may be supplied separately and/or alternately.

When the gas phase catalytic reaction is conducted using an alkane and ammonia substantially free from molecular oxygen, as the feed gas, it is advisable to employ a method wherein a part of the catalyst is periodically withdrawn and sent to an oxidation regenerator for regeneration, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

This aspect of the present invention will be described in further detail with respect to a case where propane is used as the starting material alkane and air is used as the oxygen source. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of the propane. The proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes, the composition of the feed gas may be selected in accordance with the conditions for propane.

The process of the second aspect of the present invention may be conducted at a temperature of, for example, from 250° C. to 480° C. More preferably, the temperature is from 300° C. to 400° C. The gas space velocity, SV, in the gas phase reaction is usually within the range of from 100 to 10,000 $hr^{-1}$, preferably from 300 to 6,000 $hr^{-1}$, more preferably from 300 to 2,000 $hr^{-1}$. As a diluent gas, for adjusting the space velocity and the oxygen partial pressure, an inert gas, such as carbon dioxide, nitrogen, argon or helium, can be employed. When ammoxidation of propane is conducted by the method of the present invention, in addition to acrylonitrile, carbon monoxide, carbon dioxide, acetonitrile, hydrocyanic acid and acrolein may form as by-products.

Propene is also formed as a reaction by-product. The unreacted propane and by-product propene are recovered from the effluent stream exiting the gas phase catalytic oxidation reactor and are recycled to the reactor. Recovery of the unreacted propane and by-product propene from the reactor effluent stream may be effected by conventional techniques for the recovery of hydrocarbon streams. For example, acrylonitrile and oxygenated by-products of the reaction (including $CO_2$ and CO (after being oxidized to $CO_2$)) may be scrubbed from the effluent stream by utilization of suitable solvent(s) in one or more "scrubbers" or absorption towers; and the hydrocarbon components of the effluent stream may be adsorbed in one or more adsorption beds which selectively adsorb the hydrocarbons and, subsequently, are desorbed and sent to the reactor feed.

In order to improve the yield over and above that achieved by the use of recycled propene, it is also possible to use a reactor configuration wherein the reactor comprises at least two sub-zones, the sub-zones being disposed sequentially so that the reactants pass through the sub-zones in sequential order. At least two of the sub-zones are at different temperatures. Preferably, the higher temperature is upstream of the lower temperature, i.e. the higher temperature sub-zone precedes the lower temperature sub-zone in the sequence. In this regard, the temperatures may be controlled by providing separate temperature control systems for the at least two sub-zones.

Alternatively, another technique for increasing the yield over and above that achieved by the use of the recycled propene is to once again use a reactor configuration wherein the reactor comprises at least two sub-zones, the sub-zones being disposed sequentially so that the reactants pass through the sub-zones in sequential order. However, in this embodiment, at least two of the sub-zones contain different concentrations of the catalyst containing a mixed metal oxide. Preferably, the lower concentration of catalyst is downstream of the higher concentration of catalyst, i.e. the higher concentration of catalyst sub-zone precedes the lower concentration of catalyst sub-zone in the sequence. In this regard, the concentration of catalyst could be controlled by diluting the catalyst with an inert solid, e.g., physically mixing the catalyst with an inert solid, or, if the catalyst is a supported catalyst, changing the concentration of the catalyst on the support.

The mixed metal oxide having the formula $A_aM_mN_nX_xO_o$, prepared in the manner as described above, has adequate catalytic activity by itself. However, in order to further improve the selectivity and yield of the nitrile, it is particularly preferred to use a catalyst having a certain specific oxide incorporated therein. As such a specific oxide, it is possible to employ an oxide containing at least one member selected from the group consisting of antimony, bismuth, cerium and boron. An antimony oxide is particularly preferred.

The antimony oxide may, for example, be an antimony oxide such as $Sb_2O_3$, $Sb_2O_4$ or $Sb_2O_5$, or it may be a complex antimony oxide, e.g., $SbO_2 \cdot (Sb_2O_4)$. These oxides may be used alone or in combination as a mixture of a plurality of them. Alternatively, the oxide may be used in the form of a hydrate. Further, in some cases, it is possible to employ as a solid catalyst a substance prepared by incorporating an organic compound containing antimony, such as ammonium antimony tartarate or antimony oxalate, in the mixed metal oxide, followed by calcination. In this case, the organic compound containing antimony will be converted to antimony oxide by the calcination.

The bismuth oxide to be incorporated may, for example, be a bismuth oxide such as $Bi_2O_3$ or $Bi_2O_4$, and it may also be a hydrate such as $Bi_2O_4.2H_2O$. These oxides may be used alone or in combination as a mixture of a plurality of them. In some cases, a salt of an organic or inorganic acid or a hydroxide containing bismuth, such as bismuth hydroxide, bismuth nitrate, bismuth nitrate oxide or bismuth acetate, may be added to the mixed metal oxide, followed by calcination, and the substance thereby obtained can be used as a solid catalyst. In this case, the salt or the hydroxide containg bismuth will be converted to bismuth oxide by the calcination.

The cerium oxide may, for example, be a cerium oxide such as $Ce_2O_3$ or $CeO_2$. These oxides may be used alone or in combination as a mixture of a plurality of them. In some cases, a salt of an organic or inorganic acid or a hydroxide containing cerium, such as cerium nitrate, cerium hydroxide, cerium oxalate or cerium acetate, may be added to the mixed metal oxide, followed by calcination, and the product of the calcination can be used as a solid catalyst. In this case, the salt or the hydroxide containing cerium will be converted to cerium oxide by the calcination.

The boron oxide is usually $B_2O_3$. However, a boric acid or a boric acid ester, such as orthoboric acid, metaboric acid, ethyl borate or propyl borate, may be added to the mixed metal oxide, followed by calcination, and the calcined product can be used as a solid catalyst. In such a case, the boric acid or the the boric acid ester is believed to be converted to boron oxide by the calcination.

As a method for incorporating the above-mentioned specific oxides into the mixed metal oxide, it is advisable to pulverize and mix both materials so that the contact of the specific oxide with the mixed metal oxide can be effectively done. The weight ratio of the specific oxide to the mixed metal oxide is usually from 0.0001 to 0.2, preferably from 0.001 to 0.05. After the addition, the mixture may be used as it is for the reaction to produce a nitrile. However, in order to effectively obtain the benefit of the addition of the specific oxide, it is preferred to calcine the mixture again at a temperature of from 300° C. to 650° C., preferably from 350° C. to 600° C., usually for from 0.5 to 30 hours, preferably from 1 to 10 hours. The atmosphere for the calcination is not particularly limited, but it is usually preferred to employ an inert gas atmosphere such as nitrogen, argon or helium, and the inert gas may further contain a reducing gas such as hydrogen, ammonia or a hydrocarbon, or steam. Otherwise, the calcination may be conducted under vacuum.

Even if the specific oxide is added to the mixed metal oxide, followed by mixing and calcination, the X-ray diffraction pattern of the obtained product is substantially the same as that of the mixed metal oxide before the addition of the specific oxide, and there is no substantial change observed in the crystal structure.

The so-formed catalyst may be used alone, however, it may also be used together with a conventional carrier such as silica, alumina, titania, aluminosilicate or diatomaceous earth. Further, depending upon the scale or system of the reaction, it may be molded into a proper shape and/or particle size.

EXAMPLES

The following definitions apply to the Comparative Examples and the Example:
(1) Conversion (%)=(moles of consumed hydrocarbon/moles of supplied hydrocarbon)×100;
(2) Selectivity (%)=(moles of formed product/moles of consumed hydrocarbon)×100;
(3) Yield (%)=(moles of formed product/moles of supplied hydrocarbon)×100.

Comparative Example 1

Conversion of a pure propene feed to acrylic acid, by oxidation with air in the presence of steam, over a mixed metal oxide catalyst, prepared in accord with the present invention, and containing Mo, V, Te and Nb as essential components, was effected in a single pass at various temperatures and reaction times. The results are shown in the following Table 1.

TABLE 1

| Temperature ° C. | Reaction Time (sec) | Conversion (%) | Acrylic Acid Selectivity (%) | Acetone Selectivity (%) | Acrylic Acid Yield (%) |
|---|---|---|---|---|---|
| 240 | 3 | 90 | 26.4 | 37 | 23.8 |
| 320 | 3 | 100 | 66.1 | 0.3 | 66.1 |
| 350 | 1 | 100 | 75.3 | 0.2 | 75.3 |
| 350 | 0.5 | 87 | 81.7 | 3 | 71.1 |

Comparative Example 2

Conversion of a pure propane feed to acrylic acid and propene, by oxidation with oxygen in the presence of steam and nitrogen (to simulate carbon oxides and other impurities), over the mixed metal oxide catalyst as prepared in Comparative Example 1, was effected in a single pass using a feed comprising 47 mole % propane, 19 mole % oxygen, 20 mole % steam and 14 mole % nitrogen, a reaction time of 3 seconds and reaction temperatures of 332° C. and 343° C. The results are shown in Table 2.

TABLE 2

| Temperature (° C.) | Propane Conversion (%) | Acrylic Acid Selectivity (%) | Propene Selectivity (%) |
|---|---|---|---|
| 332 | 13.6 | 51 | 23 |
| 343 | 15.1 | 50 | 22 |

Example 1

Conversion of a C3 hydrocarbon feed to acrylic acid and propene, by oxidation with air in the presence of steam, over the mixed metal oxide as prepared in Comparative Example 1, may be effected at 350° C. and a reaction time of 1 second, as follows:

At the outset, 100 moles of propane is fed to an oxidation reactor, containing the aforementioned catalyst, along with air and steam. After oxidation, acrylic acid, carbon oxides and other impurities are separated from the effluent stream from the reactor, while unreacted propane and product propene are recycled back as feed to the oxidation reactor.

Fresh propane feed is added to maintain a constant 100 moles of C3 hydrocarbon feed and the system is allowed to equilibrate. At equilibrium, the system yields 9.4 moles of acrylic acid and 12.3 moles (4.1 moles of C3 hydrocarbon converted to $CO_x$) carbon oxides, while recycling back 83.1 moles of unreacted propane and 3.4 moles of product propene. Fresh feed addition is 13.5 moles of propane.

Under these recycle conditions, the yield of acrylic acid based on the fresh propane feed is 9.4 moles of acrylic acid/13.5 moles of fresh propane, i.e. 70%.

What is claimed is:

1. A method for producing an unsaturated carboxylic acid comprises:
   (a) contacting, in a reaction zone, an alkane with a catalyst containing a mixed metal oxide, under conditions which produce a product gas comprising said unsaturated carboxylic acid, unreacted alkane and a product alkene; (b) recovering unreacted alkane and product alkene from said product gas; and (c) recycling said recovered unreacted alkane and product alkene to said reaction zone, said reaction zone comprising at least two sub-zones which are disposed sequentially relative to one another, wherein said alkane passes through said sub-zones in sequential order;
   wherein each of said at least two sub-zones contains said catalyst which contains said mixed metal oxide which consists of a material having the formula $A_aM_mN_nX_xO_o$ wherein A is at least one element selected from the group consisting of molybdenum and tungsten, wherein M is at least one element selected from the group consisting of vanadium, cerium and chromium, wherein N is at least one element selected from the group consisting of tellurium, bismuth and selenium, wherein X is at least one element selected from the group consisting of niobium, tantalum, titanium, aluminum, zirconium, chromium, manganese, iron, ruthenium, cobalt, rhodium, nickel, platinum, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium, wherein $0.25<a<0.98$, $0.003<m<0.5$, $0.003<n<0.5$, $0.003<x<0.5$ and o is dependent on the oxidation state of the other elements, and wherein said catalyst in each of said at least two sub-zones has the same composition and catalyzes the conversion of said alkane to said unsaturated carboxylic acid.

2. The method according to claim 1, wherein said contact, in said reaction zone, of said alkane and said catalyst is carried out in the further presence of steam.

3. The method according to claim 2, wherein said contact, in said reaction zone, is carried out in the further presence of oxygen and, optionally, an inert diluting gas; and wherein the molar ratio of (alkane or alkane plus alkene):(oxygen):(diluting gas):(steam) being fed to said reaction zone is (1):(0.1 to 10):(0 to 20):(0.2 to 70).

4. The method according to claim 1, wherein the mixed metal oxide exhibits X-ray diffraction peaks at the following diffraction angles 2θ in the X-ray diffraction pattern using Cu—Kα radiation:

Diffraction angle 2θ (±0.3°)
22.1°,
28.2°,
36.2°,
45.2°,
50.0°.

5. The method according to claim 1, wherein at least two of said sub-zones being at different temperatures.

6. The method according to claim 5, wherein, of said at least two sub-zones at different temperatures, the first of said at least two sub-zones at different temperatures in the sequence is at a higher temperature than the second of said at least two sub-zones at different temperatures in the sequence.

7. The method according to claim 1, wherein at least two of said sub-zones containing different concentrations of said catalyst containing a mixed metal oxide.

8. The method according to claim 7, wherein, of said at least two sub-zones containing different concentrations of said catalyst containing a mixed metal oxide, the first of said at least two sub-zones containing different concentrations of said catalyst in the sequence has a higher concentration of said catalyst than the second of said at least two sub-zones containing different concentrations of said catalyst in the sequence.

9. A method for producing an unsaturated nitrile comprises:
   (a) contacting, in a reaction zone, an alkane and ammonia in the presence of a catalyst containing a mixed metal oxide, under conditions which produce a product gas comprising said unsaturated nitrile, unreacted alkane and a product alkene; (b) removing unreacted alkane and product alkene from said product gas; and (c) recycling said removed unreacted alkane and product alkene to said reaction zone, said reaction zone comprising at least two sub-zones which are disposed sequentially relative to one another, wherein said alkane passes through said sub-zones in sequential order;
   wherein each of said at least two sub-zones contains said catalyst which contains said mixed metal oxide which has the formula $A_aM_mN_nX_xO_o$ wherein A is at least one element selected from the group consisting of molybdenum and tungsten, wherein M is at least one element selected from the group consisting of vanadium, cerium and chromium, wherein N is at least one element selected from the group consisting of tellurium, bismuth, antimony and selenium, wherein X is at least one element selected from the group consisting of niobium, tantalum, titanium, aluminum, zirconium, chromium, manganese, iron, ruthenium, cobalt, rhodium, nickel, platinum, bismuth, boron, indium, arsenic, germanium, tin, lithium, sodium, potassium, rubidium, cesium, francium, beryllium, magnesium, calcium, strontium, barium, hafnium, lead, phosphorus, promethium, europium, gadolinium, dysprosium, holmium, erbium, thulium, ytterbium, lutetium, gold, silver, palladium, gallium, zinc, praseodymium, rhenium, iridium, neodymium, yttrium, samarium and terbium, wherein $0.25<a<0.98$, $0.003<m<0.5$, $0.003<n<0.5$, $0.003<x<0.5$ and o is dependent on the oxidation state of the other elements, and wherein said catalyst in each of said at least two sub-zones has the same composition and catalyzes the conversion of said alkane to said unsaturated nitrile.

10. The method according to claim 9, wherein the mixed metal oxide exhibits X-ray diffraction peaks at the following diffraction angles 2θ in the X-ray diffraction pattern using Cu—Kα radiation:

Diffraction angle 2θ (±0.3°)
   22.1°,
   28.2°,
   36.2°,
   45.2°,
   50.0°.

11. The method according to claim 9, wherein at least two of said sub-zones being at different temperatures.

12. The method according to claim 11, wherein, of said at least two sub-zones at different temperatures, the first of said at least two sub-zones at different temperatures in the sequence is at a higher temperature than the second of the said at least two sub-zones at different temperatures in the sequence.

13. The method according to claim 9, wherein at least two of said sub-zones containing different concentrations of said catalyst containing a mixed metal oxide.

14. The method according to claim 13, wherein, of said at least two sub-zones containing different concentrations of said catalyst containing a mixed metal oxide, the first of said at least two sub-zones containing different concentrations of said catalyst in the sequence has a higher concentration of said catalyst than the second of said at least two sub-zones containing different concentrations of said catalyst in the sequence.

* * * * *